(12) United States Patent
Dawson

(10) Patent No.: US 11,684,450 B2
(45) Date of Patent: Jun. 27, 2023

(54) DISTAL TIP PROTECTOR FOR USE IN PRE-TREATING MEDICAL INSTRUMENTS

(71) Applicant: MEDISAFE UK LIMITED, Bishop's Stortford (GB)

(72) Inventor: Lawrence Ralph Dawson, Essex (GB)

(73) Assignee: Medisafe UK Limited, Bishops Stratford (GB)

( * ) Notice: Subject to any disclaimer, the term of this patent is extended or adjusted under 35 U.S.C. 154(b) by 1130 days.

(21) Appl. No.: 14/428,029

(22) PCT Filed: Sep. 13, 2013

(86) PCT No.: PCT/GB2013/052409
§ 371 (c)(1),
(2) Date: Mar. 13, 2015

(87) PCT Pub. No.: WO2014/041369
PCT Pub. Date: Mar. 20, 2014

(65) Prior Publication Data
US 2015/0250550 A1    Sep. 10, 2015

Related U.S. Application Data

(60) Provisional application No. 61/701,052, filed on Sep. 14, 2012.

(30) Foreign Application Priority Data

Sep. 14, 2012 (GB) ..................................... 1216460

(51) Int. Cl.
*A61B 90/70* (2016.01)
*A61B 50/39* (2016.01)
(Continued)

(52) U.S. Cl.
CPC .............. *A61B 90/70* (2016.02); *A61B 50/36* (2016.02); *A61B 50/39* (2016.02); *B08B 3/106* (2013.01);
(Continued)

(58) Field of Classification Search
CPC ......... A61B 19/34; A61B 90/70; A61B 50/36; A61B 50/39; A61B 2090/701;
(Continued)

(56) References Cited

U.S. PATENT DOCUMENTS 2,803,252 A    8/1957  Bloome
4,362,241 A   12/1982  Williams
(Continued)

FOREIGN PATENT DOCUMENTS

CN    2287477    8/1988    .............. A61L 2/18
CN    2287477    8/1998
(Continued)

OTHER PUBLICATIONS

German Office Action from corresponding German Patent Application DE 112013003028.4, dated May 30, 2016.
(Continued)

*Primary Examiner* — David G Cormier
(74) *Attorney, Agent, or Firm* — Kusner & Jaffe

(57) ABSTRACT

A method of pre-treating a contaminated medical instrument that is to undergo decontamination involves inserting a distal tip of the instrument into a distal tip protector. The distal tip of the instrument is inserted through a rupturable resilient seal into an internal cavity of the protector that contains a fluid. The distal tip protector thereby maintains a fluid around the distal tip of the instrument until the distal tip protector is removed to allow reprocessing of the instrument to take place, facilitating decontamination of the instrument.

15 Claims, 3 Drawing Sheets

(51) Int. Cl.
*A61B 50/36* (2016.01)
*B08B 3/10* (2006.01)
*A61B 90/00* (2016.01)

(52) U.S. Cl.
CPC ......... *A61B 2090/0813* (2016.02); *B08B 3/10* (2013.01); *Y10T 29/49826* (2015.01)

(58) Field of Classification Search
CPC .......... A61B 2090/0813; A61B 50/362; A61B 1/121; A61B 1/122; A61B 1/123; B08B 3/106; Y10T 29/49826; A61M 5/3205; A61M 39/16; A61M 39/165; A61C 19/002; A61L 2/18; A61L 2202/24
See application file for complete search history.

(56) References Cited

U.S. PATENT DOCUMENTS

| | | | |
|---|---|---|---|
| 4,446,967 A | 5/1984 | Halkyard | |
| 4,748,007 A | 5/1988 | Gaudion et al. | |
| 4,813,538 A | 3/1989 | Blackman | |
| 4,845,923 A * | 7/1989 | Donovan | A61M 5/3205 53/431 |
| 5,038,929 A * | 8/1991 | Kubofcik | A61M 5/3205 206/210 |
| 5,308,406 A * | 5/1994 | Wallock | A61L 2/18 134/42 |
| 5,429,118 A * | 7/1995 | Cole | A61B 1/00142 600/121 |
| 5,447,684 A | 9/1995 | Williams | |
| 5,705,134 A | 1/1998 | Biagi | |
| 5,707,173 A * | 1/1998 | Cottone | A61M 5/3205 206/366 |
| 5,755,894 A | 5/1998 | Bowman et al. | |
| 5,902,547 A | 5/1999 | Hill et al. | |
| 5,904,677 A * | 5/1999 | Drummey | A61B 10/0096 215/247 |
| 5,944,179 A * | 8/1999 | Walker | B65D 59/06 206/305 |
| 6,053,314 A * | 4/2000 | Pittman | A61M 5/3205 206/366 |
| 6,245,053 B1 * | 6/2001 | Benjamin | A61M 25/0014 264/345 |
| 6,361,744 B1 * | 3/2002 | Levy | B01L 3/50825 215/247 |
| 6,527,872 B1 | 3/2003 | Fricker | |
| 8,734,730 B2 | 5/2014 | Soltz et al. | 422/300 |
| 8,824,391 B2 | 9/2014 | Yang et al. | H04L 25/0226 |
| 9,155,809 B2 * | 10/2015 | Roberts | A61L 2/18 |
| 2002/0159917 A1 | 10/2002 | Swart et al. | |
| 2003/0111361 A1 | 6/2003 | Fischer et al. | |
| 2003/0191390 A1 | 10/2003 | Murakami | 600/439 |
| 2006/0116551 A1 | 6/2006 | Lovett et al. | |
| 2009/0241987 A1 * | 10/2009 | Serizawa | A61L 2/18 134/1 |
| 2011/0028790 A1 * | 2/2011 | Farr | A61B 1/00052 600/187 |
| 2012/0022400 A1 | 1/2012 | Mumaw | |
| 2013/0068247 A1 | 3/2013 | Batchelor et al. | |

FOREIGN PATENT DOCUMENTS

| | | | |
|---|---|---|---|
| CN | 201710684 | 1/2011 | ............... A61L 2/18 |
| DE | 3416743 | 7/1985 | ............... A61L 2/18 |
| DE | 3713899 | 8/1988 | ............... B08B 3/00 |
| DE | 3416743 | 10/1989 | |
| DE | 202012002701 U1 | 6/2012 | |
| EP | 2478829 | 7/2012 | ............... A61B 1/31 |
| FR | 2600536 | 12/1987 | ............... A61L 2/18 |
| GB | 2404857 | 8/2006 | |
| GB | 2456323 | 7/2009 | |
| JP | 02140168 | 5/1990 | ............... A61L 2/18 |
| JP | 2003-299666 | 10/2003 | ............. A61B 18/00 |
| JP | 2008-253755 | 10/2008 | ............. A61B 17/00 |
| JP | 2011-143179 | 7/2011 | ............... A61B 1/12 |
| JP | 5228114 | 7/2013 | ............ H04W 72/04 |

OTHER PUBLICATIONS

Japanese Office Action from corresponding Japanese Patent Application No. JP 2015-531641, dated Feb. 23, 2016 (with English translation).
International Search Report from corresponding International Patent Application No. PCT/GB2013/052409, dated Nov. 20, 2013.
Written Opinion of the International Searching Authority from corresponding International Patent Application No. PCT/GB2013/052409, dated Nov. 20, 2013.
United Kingdom Office Action from corresponding GB 1216460.4, dated Jan. 14, 2013.
Search Report.
Search Report—United Kingdom.
JP02140168—English Abstract.
German Office Action.
Japanese Office Action.
United Kingdom Office Action from corresponding GB 1421460.5, dated Dec. 31, 2014.
United Kingdom Office Action from corresponding GB 1421460.5, dated Mar. 4, 2015.
United Kingdom Office Action from corresponding GB 1511710.4, dated Dec. 22, 2015.
German Office Action from corresponding German Patent Application DE 112013003028.4, dated May 26, 2015.
Japanese Office Action from corresponding Japanese Patent Application No. JP 2016-163896, dated Oct. 17, 2016 (with English translation).
Office Action issued in corresponding European Patent Application No. 13 763 292.3 dated Feb. 23, 2018.
European Office Action issued in connection with corresponding EP 13763292.3, dated Oct. 7, 2019.
Office Action dated Apr. 3, 2020 in related/corresponding U.S. Appl. No. 15/597,398, filed Mar. 3, 2015.

* cited by examiner

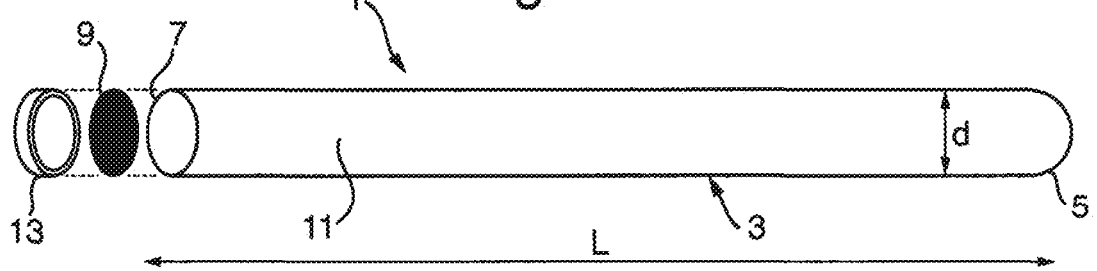
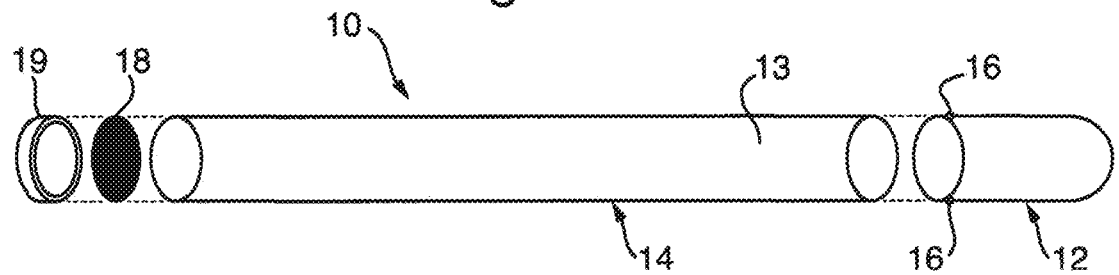
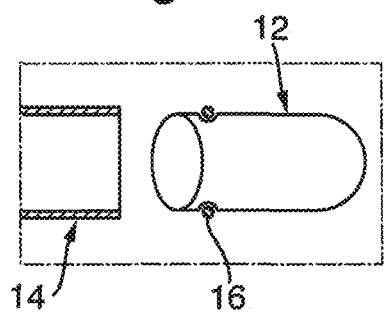
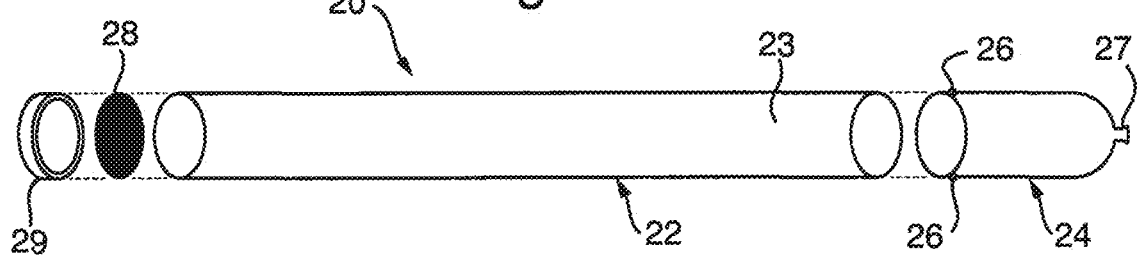

DISTAL TIP PROTECTOR FOR USE IN PRE-TREATING MEDICAL INSTRUMENTS

BACKGROUND

The present invention relates to a method of pre-treating a medical instrument that is to undergo reprocessing e.g. decontamination. The present invention also relates to a distal tip protector for use in the pre-treatment of a medical instrument that is to undergo reprocessing.

The invention is particularly, although not exclusively, applicable to a method of pre-treating a surgical instrument. However the methods of the present invention are also applicable to the pre-treatment of other types of medical instrument, or other medical or surgical equipment or components prior to reprocessing. The methods of the present invention are applicable to the pre-treatment of medical instruments for use in any medical field, including dental and veterinary fields.

The present invention relates to the pre-treatment of medical instruments prior to reprocessing e.g. decontamination of the instrument. Reprocessing may refer to any step or steps that are performed to render a medical instrument that has been used suitable for further use. Although the medical instruments with which the present invention is concerned may be constructed to be non-disposable, the present invention may also be used in conjunction with disposable instruments, which in many cases are too expensive to be disposed of after a single use. For example, the invention may be used to protect the tips of so-called "reposable" instruments prior to reprocessing, which are limited to a certain number of uses e.g. 10 uses. Thus, the methods of the present invention may be applied to any medical instrument which is to undergo reprocessing, including non-disposable, disposable or semi-disposable or reposable instruments. Thus, the invention is broadly applicable to pre-treating a reusable medical instrument.

Reprocessing of an instrument may involve any process or processes to render the used medical instrument suitable for reuse. Reprocessing may involve any type or types of decontaminating process e.g. deluge decontamination, soaking, ultrasonic decontamination, disinfection, sterilisation or other cleaning process. Reprocessing may involve automatic and/or manual steps.

Medical instruments have become increasingly complex in recent years, particularly at the distal or working end. For example, instruments may have a wrist like mechanism at the distal working end that may be controlled remotely by a surgeon to provide greater dexterity and access to parts of a body for surgery. Examples of instruments which may have relatively complex distal ends include instruments for robot assisted surgery, incisionless surgery, laparoscopic surgery, minimally invasive surgery or so-called "NOTES" (Natural Orifice Transluminal Endoscopic Surgery).

In many cases it is not viable to dispose of such instruments after a single use, and the instruments undergo reprocessing after use to enable them to be used again. Achieving adequate decontamination of the complex distal ends of such instruments presents considerable challenges. During use, the distal end of the instrument will come into contact with substances such as blood, tissue or other materials. More complex instruments present a greater number of surfaces and/or crevices which may become contaminated by such materials, and there may be considerable challenges in ensuring that these are properly removed during reprocessing. The problem is exacerbated as instruments are often not reprocessed immediately after use. For example, there may be some delay between an instrument being used in a surgical procedure, and being processed at a reprocessing facility, ranging from hours to even a day or more. This is due to the time involved in transporting instruments from the location of use to a reprocessing facility, and potentially due to delays in reprocessing taking place at the facility e.g. due to workload, due to holiday periods etc. Delays in commencing reprocessing of instruments may allow blood, tissue and other materials to become dried to the instrument, making them still more difficult to remove.

The present invention may, at least in preferred embodiments, address at least some of these problems.

SUMMARY

In accordance with a first aspect, there is provided a method of pre-treating a contaminated medical instrument that is to undergo reprocessing, the method comprising:

applying a distal tip protector to a distal tip of the instrument;

and using the distal tip protector to maintain fluid around the distal tip of the instrument while the distal tip is located within the distal tip protector.

The present invention also extends to a distal tip protector for use in the pre-treatment of a contaminated medical instrument that is to undergo reprocessing. In accordance with a further aspect, there is provided a distal tip protector for use in pre-treating a contaminated medical instrument that is to undergo reprocessing, the distal tip protector comprising; means for maintaining fluid around the distal tip of a medical instrument inserted in the distal tip protector when the distal tip protector is applied to a distal tip of an instrument in use.

This further aspect may include any or all of the features described by reference to any of the other aspects or embodiments. The distal tip protector may include any of the features described by reference to the method aspects, and the method aspects may include any of the features described by reference to the distal tip protector and vice versa.

A distal tip protector is applied to the distal tip of a contaminated instrument to be reprocessed, and the distal tip protector is used to maintain fluid around the distal tip of the instrument located therein. The distal tip protector cooperates with the instrument to maintain fluid in contact with the distal tip of the instrument. In this way, the distal tip of the instrument is kept wet, which may maintain any tissue, blood or other contaminants at the distal tip moist, so that they may subsequently be more easily removed when the instrument undergoes reprocessing. In addition, the distal tip protector protects the distal tip of the instrument during transport or storage prior to reprocessing. This may help to protect any delicate mechanism at the distal tip.

The Applicant has thus realised that a distal tip protector may be used to not only protect the distal tip of a medical instrument prior to reprocessing, but may simultaneously provide the ability to pre-treat the distal tip by maintaining a fluid around the tip to facilitate subsequent reprocessing of the instrument. The user may simply locate the distal tip protector over the distal tip of the instrument, if necessary supplying a fluid thereto before or after applying the protector to the distal tip (if the protector is not pre-filled), to provide the pre-cleaning step.

In accordance with embodiments of the invention, the distal tip of the instrument is releasably retained by the distal tip protector applied thereto, and the method comprises using the distal tip protector to maintain fluid around the distal tip of the instrument while the distal tip of the instrument is retained by the distal tip protector. The distal tip is retained within the distal tip protector. The distal tip protector may be configured to releasably retain a distal tip of an instrument therein in use. In embodiments the distal tip protector is configured to cooperate with the instrument to releasably retain the distal tip thereof within the distal tip protector. This may be achieved in any suitable manner. The distal tip protector may provide a removable cap for the instrument.

The medical instrument to whose distal tip the distal tip protector is applied is a contaminated instrument that is to undergo reprocessing. The method of the present invention is a method of pre-treating the medical instrument before reprocessing occurs. The method may be carried out before any reprocessing e.g. decontamination occurs. Thus, the steps of applying the distal tip protector to the distal tip of the instrument and using the distal tip protector to maintain fluid around the distal tip of the instrument are carried out prior to reprocessing of the instrument. In accordance with the invention in any of its embodiments the method may comprise using the distal tip protector to maintain fluid around the distal tip of the instrument before and/or until the instrument undergoes reprocessing. The distal tip protector may be used to continually maintain fluid around the distal tip of the instrument until the instrument undergoes reprocessing. In other arrangements, the distal tip protector may be used to maintain fluid around the distal tip of the instrument for only part of a period until the instrument undergoes reprocessing. The distal tip protector may be used to maintain fluid around the distal tip after or simultaneously with being applied to the distal tip of the instrument e.g. depending upon whether it is pre-filled as discussed below. The pre-treatment of the present invention is preferably carried out before the instrument undergoes any decontamination process. The instrument is not used again in a medical procedure after the pre-treatment and before reprocessing e.g. decontamination.

In some embodiments the method comprises leaving the distal tip protector applied to the distal tip of the instrument for maintaining fluid around the distal tip of the instrument until the instrument undergoes reprocessing. The distal tip protector may be kept on the distal tip of the instrument continually until reprocessing commences.

The method may comprise using the distal tip protector to maintain fluid around the distal tip of the instrument during storage and/or transport of the instrument prior to reprocessing e.g. decontamination. The method may comprise applying the distal tip protector to the distal tip of the instrument and using the distal tip protector to maintain fluid around the distal tip of the instrument at a first location e.g. a location of use of the instrument. The location may be an operating theatre. The first location may be a location different to a location at which the instrument is to undergo reprocessing. The distal tip protector may be left applied to the distal tip of the instrument maintaining fluid around the distal tip until the instrument reaches a second location e.g. a reprocessing facility location.

The method may further comprise removing the distal tip protector from the distal tip of the instrument. The step of removing the distal tip protector from the distal tip of the instrument may be carried out at a reprocessing facility. The step of removing the distal tip of the instrument from the distal tip protector may be carried out at a different location to the location at which the distal tip is inserted in the distal tip protector. The distal tip protector is removed from the distal tip of the instrument before the instrument is subjected to reprocessing e.g. decontamination.

The method may further comprise subjecting the instrument to one or more reprocessing steps after removal of the distal tip protector from the distal tip of the instrument. In embodiments in which the instrument is subjected to one or more reprocessing steps, the one or more reprocessing steps preferably comprise one or more decontaminating steps. In general, a reference herein to the instrument being an instrument that is to undergo reprocessing refer to an instrument that is to undergo one or more reprocessing steps that may be of any of the types which will be described, and which preferably comprise or are decontaminating steps. The reprocessing e.g. decontaminating steps that the instrument is to undergo or undergoes are preferably selected from cleaning, disinfection or sterilisation steps or combinations thereof. Cleaning steps may comprise one or more of deluge decontamination, ultrasonic decontamination, soaking and internal flushing steps.

The one or more reprocessing steps may be automated reprocessing steps and/or manually performed reprocessing steps. In some embodiments the step of subjecting the instrument to one or more reprocessing steps comprises locating the instrument in an automated decontaminating apparatus, and the reprocessing step(s) that the instrument is to undergo may comprise such steps. The method may comprise subjecting the instrument to an automated decontaminating cycle of the apparatus. The cycle may include one or more of deluge decontamination, ultrasonic decontamination, internal flushing, disinfection, sterilisation or soaking. The apparatus may be configured to perform a single type of decontamination step or a combination of different steps e.g. in an automated cycle.

Reprocessing may comprise further steps e.g. drying packaging, inspection, assembly of the instrument, disassembly of the instrument etc.

The medical instrument subjected to the method of pre-treatment of the present invention in any of its aspects or embodiments is a contaminated instrument that is to undergo reprocessing prior to reuse. The instrument is preferably an instrument that has been used in a medical procedure. The instrument is preferably a surgical instrument that has been used in a surgical procedure. In accordance with the invention of any of its embodiments the method preferably comprises applying the distal tip protector to the distal tip of the instrument and using the distal tip protector to maintain fluid around the distal tip of the instrument after use of the instrument in a medical procedure.

In general the method of the present invention may provide a method of and distal tip protector for use in pre-treating a contaminated instrument prior to decontamination of the instrument, and references to the instrument being an instrument that is to undergo or undergoes reprocessing may be replaced by references to an instrument that is to undergo decontamination.

In accordance with a further aspect of the invention there is provided a method of pre-treating a contaminated medical instrument that is to undergo decontamination, the method comprising;

applying a distal tip protector to a distal tip of the instrument;

wherein the method comprises using the distal tip protector to maintain fluid around the distal tip of the instrument while the distal tip is located within the distal tip protector.

In accordance with a further aspect of the invention there is provided a distal tip protector for use in pre-treating a contaminated medical instrument that is to undergo decontamination, the distal tip protector comprising; means for maintaining fluid around the distal tip of a medical instrument inserted in the distal tip protector when the distal tip protector is applied to a distal tip of an instrument in use.

The present invention in this further aspect may include any of the features described in accordance with the invention in the other aspects described.

In accordance with the invention in any of its aspects, the method of the present invention preferably comprises applying the distal tip protector to the distal tip of the instrument and using the distal tip protector to maintain fluid around the distal tip of the instrument after use of the instrument in a medical procedure and/or before and/or until the instrument undergoes reprocessing or decontamination.

The step of applying the distal tip protector to the distal tip of the instrument may be carried out in any manner. In preferred embodiments the step comprises inserting the distal tip of the instrument into the distal tip protector, and the step of applying the distal tip protector referred to herein may be replaced by a reference to such a step. The step of applying the distal tip protector to the distal tip may comprise sliding the distal tip protector over the distal tip of the instrument. This may be accomplished in a similar manner to locating a cap over the end of the instrument. However, the distal tip protector of the present invention provides the added function of pre-treating the distal tip prior to reprocessing by bringing a fluid into contact with the contaminated instrument. The instrument may be contaminated at least at the distal tip thereof. The method may comprise using the distal tip protector to provide a pre-soaking of the distal tip of the instrument. The method preferably does not comprise supplying fluid to the interior of the instrument while the distal tip is located in the distal tip protector.

In accordance with a further aspect of the invention there is provided a method of pre-treating a contaminated medical instrument that is to undergo decontamination, the method comprising;

inserting a distal tip of the instrument into a distal tip protector;

wherein the method comprises using the distal tip protector to maintain fluid around the distal tip of the instrument while the distal tip is located within the distal tip protector.

The present invention in this further aspect may include any of the features described in respect to other aspects of the invention to the extent they are not mutually exclusive.

In accordance with the invention in any of its aspects, the distal tip protector once applied to the distal tip of an instrument is movable with the instrument. The protector allows pre-cleaning to be carried out as the instrument is moved from one location to another. The distal tip protector is portable.

In embodiments the distal tip protector provides a self contained unit for maintaining fluid around the distal tip of the instrument inserted therein.

The method may extend to the step of providing the distal tip protector and/or the contaminated medical instrument.

The distal tip protector is applied to, and where appropriate, removed from the distal tip of the instrument by a user. The distal tip protector is arranged to be manually applied to or removed from the distal tip of an instrument. The distal tip protector of the invention in any of its embodiments is preferably a hand held distal tip protector.

The distal tip protector is used in accordance with the invention in any of its aspects to maintain fluid around the distal tip of the instrument while the distal tip of the instrument is located in the distal tip protector. It will be appreciated that the step of applying the distal tip protector to the distal tip of the instrument comprises applying the distal tip protector to the distal tip of the instrument such that the distal tip of the instrument is located within the distal tip protector. The distal tip protector receives the distal tip of the instrument. This may be achieved in any suitable manner.

The distal tip protector cooperates with the instrument while the distal tip of the instrument is located in the distal tip protector to maintain fluid around the distal tip of the instrument. The protector may cooperate with a shaft of the instrument to achieve this. Preferably the distal tip protector cooperates with the instrument while the distal tip of the instrument is located in the distal tip protector to maintain fluid around the distal tip of the instrument and to releasably retain the distal tip of the instrument located in the distal tip protector. The distal tip protector cooperates with the instrument to releasably retain the distal tip of the instrument located in the distal tip protector with fluid therearound. The distal tip protector maintains fluid around the exterior of the distal tip, and preferably does not provide fluid to the interior of the instrument. Cooperation to releasably retain the instrument and/or to maintain fluid around the tip may be with a part of the instrument proximal to the distal tip. The cooperation may be with a shaft of the instrument to which the distal tip is connected.

The method may comprise using the distal tip protector to maintain a fluid around the distal tip of an instrument inserted in the distal tip protector such that the fluid surrounds the distal tip of the instrument. The fluid may surround the distal tip on all sides. The fluid will then contact the distal tip on all sides.

The distal tip protector may be arranged to be able to retain a fluid in any manner when the distal tip of an instrument is inserted therein such that the fluid will contact and/or surround the distal tip. The fluid may be retained by the distal tip protector at least while the distal tip is inserted in the distal tip protector. The fluid is held in the interior of the distal tip protector.

In accordance with the invention in any of its aspects or embodiments, the distal tip protector may cooperate with the instrument to provide a container for maintaining the fluid around the distal tip of the instrument when located in the distal tip protector.

In preferred embodiments the distal tip protector comprises an internal cavity in which the distal tip is located (when the protector is applied to the distal tip), the internal cavity comprising the fluid, the distal tip protector cooperating with the instrument to maintain the fluid around the distal tip of the instrument while located in the internal cavity. The internal cavity may be a fluid holding chamber.

Preferably the distal tip protector comprises a resilient seal through which the instrument extends, the resilient seal being arranged to conform to a contour of the instrument to inhibit the leakage of fluid from the interior of the distal tip protector when the distal tip is located in the distal tip protector. The seal inhibits the leakage of fluid from the interior of the distal tip protector around the instrument i.e. around an interface between the seal and the instrument. The seal may conform to a circumferential periphery of the instrument. In preferred embodiments in which the distal tip protector comprises an internal cavity in which the distal tip is located, the resilient seal is located at an entrance to the cavity. Preferably the resilient seal is located at a proximal end of the distal tip protector, and, where appropriate, the internal cavity thereof.

The step of applying the distal tip protector to the distal tip of the instrument preferably comprises inserting the distal tip through the resilient seal into the interior of the protector or, preferably into the interior of the internal cavity thereof. In preferred embodiments the distal tip protector comprises a resilient seal at a proximal end thereof through which the distal tip of an instrument is passed into the interior of the protector. The seal is a fluid seal.

In some embodiments the resilient seal is ruptured to insert the distal tip into the distal tip protector. In some embodiments the distal tip protector thus comprises a resilient seal closing an end of the interior cavity which is ruptured when the distal tip is inserted into the distal tip protector. In other embodiments it is envisaged that the seal may comprise an aperture through which the distal tip is passed upon insertion into the distal tip protector. The seal may then provide a restriction through which the distal end of the instrument is passed. In these arrangements, the aperture may be pre-formed in the seal, or may be provided by using a seal that has previously been breached e.g. upon insertion of another instrument. Such arrangements may be applicable where the protector is filled or refilled by a user. A rupturable seal may comprise a rupturable membrane e.g. a disc of membrane.

Whether or not the seal is apertured upon insertion of the distal tip protector, the resilience of the seal allows the seal to conform to the contours of an instrument inserted therethrough to provide a barrier to the passage of fluid i.e. liquid out of the distal tip protector, to maintain fluid around the distal tip of the instrument inserted therein. In embodiments in which the seal is initially provided as a rupturable seal, the seal will additionally provide a barrier to the passage of fluid from the interior of the chamber to the exterior thereof before an instrument is inserted therethrough. This may be appropriate in arrangements in which the protector is pre-filled with a fluid before insertion of an instrument.

The seal may comprise any suitable material or materials and may be configured in any suitable manner. The seal may comprise one or more components. The seal may comprise any material or materials that may resist the passage of fluid therethrough from one side to an opposite side thereof. The degree of impermeability of the material may be chosen as desired to ensure that adequate leakage protection is provided under the conditions to be expected in use e.g. period that the protector is likely to be used for, temperature etc. For example, the seal may comprise foil, or a polymeric material or similar. In some embodiments the seal is an elastic seal. Of course, the seal need not be elastic provided that it can, to some extent, recover to continue to provide a fluid barrier sealing around the periphery of an instrument inserted in the protector. In some preferred embodiments the seal comprises a polymeric material. For example, the material may be a cling film type material.

The seal may be provided as a separate part attached to a main body of the protector or may be integrally formed therewith. The seal could be provided by a suitable configuration of a proximal end of the protector e.g. to provide a resilient fit to an instrument, or by a rupturable wall of the protector. However, preferably the seal is a separate seal attached to a main body of the protector. The seal is preferably made of a different material to the main body of the protector.

In accordance with the invention in any of its aspects or embodiments, the distal tip protector may further comprise guide means extending from the proximal end thereof for guiding an instrument during insertion of a distal tip of the instrument into the protector. The method may comprise inserting the distal tip of an instrument through the guide means and into the distal tip protector. The guide means extends proximally from the proximal end of the protector.

In embodiments the distal tip protector extends from the proximal end of the main body of the protector. The guide means may be configured to inhibit buckling of a distal tip of an instrument on insertion into the protector. In particular the guide means may be configured to inhibit buckling of a distal tip of an instrument as it is inserted through a resilient seal at a proximal end of the distal tip protector. The method may comprise inserting the distal tip of an instrument through the guide means in order to rupture the seal. The distal tip will then pass through the guide means before rupturing the seal. The guide means may guide the distal tip of the instrument as it ruptures the seal. It has been found that the distal tips of certain instruments may have a tendency to buckle when rupturing a seal e.g. when they have a joint, such as a wrist joint at the distal tip. The guide means may comprise a tube. The guide means may be chosen to have a diameter slightly greater than the diameter of an instrument with which the protector is to be used, so as to allow insertion of the distal tip therethrough, but so as to inhibit buckling of the tip. The guide means may extend a relatively short distance proximally from the proximal end of the distal tip protector. For example, the guide means may extend a distance of less than 5 cm, or in the range of from 1 cm to 5 cm. The guide means has a length that is short in comparison to a length of the protector. The guide means may remain in place after insertion of the distal tip of the instrument into the distal tip protector i.e. during use of the distal tip protector. The guide means may be attached to the distal tip protector in any suitable manner. In some preferred embodiments the guide means is attached to an end cap of the distal tip protector as discussed below.

In accordance with any of its aspects or embodiments, the distal tip protector may comprise a cap protecting the seal prior to use. The method may then comprise the step of removing the cap prior to inserting the distal tip of an instrument through the seal. Such arrangements are particularly applicable where the seal is a rupturable seal.

In other embodiments the end cap may define an aperture through which the distal tip of an instrument may be inserted into the distal tip protector. The method may comprise the step of inserting the distal tip of an instrument through the end cap and into the protector. The aperture will be a central aperture. The end cap may then remain in place during and after insertion of the distal tip of an instrument into the protector. The end cap may still act to protect the edges of a seal and maintain the seal in place in use. The end cap may, in these embodiments be in the form of an annular ring. In these embodiments the end cap may comprise guide means for guiding the distal tip of an instrument as it is inserted into the distal tip protector in accordance with any of the embodiments for the guide means discussed above. The guide means will project proximally from the end cap. The guide means may be attached to the end cap in any suitable manner e.g. being integrally moulded therewith, or may be a separate component attached thereto.

Once the instrument is inserted into the tip protector, the tip protector releasably retains the distal tip of the instrument therein. This may be achieved in any suitable manner. It will be appreciated that in embodiments having a resilient seal, the seal may also provide the function of releasably retaining the instrument with the distal tip located in the distal tip protector. The resilient seal may grip the instrument to retain the instrument with the distal tip located in the protector.

In preferred embodiments the distal tip protector comprises an interior cavity for holding fluid, and the method comprises inserting the distal tip of the instrument into the cavity and using the cavity of the distal tip protector to maintain the fluid around the distal tip of the instrument. The cavity is used to maintain fluid around the distal tip of the instrument while the distal tip is retained in the distal tip protector.

In some embodiments the distal tip protector or, in preferred embodiments, an internal cavity thereof, contains a fluid before the distal tip protector is applied to a distal tip of an instrument e.g. before the instrument is inserted into the distal tip protector, or preferably an internal cavity thereof. The method may comprise inserting the distal tip of the instrument into a fluid held in the distal tip protector or internal cavity thereof.

In these embodiments the method may comprise the step of supplying a fluid to the interior of the distal tip protector or, preferably, to an internal cavity thereof before applying the distal tip protector to the instrument e.g. before inserting the distal tip of the instrument into the distal tip protector or cavity. The fluid is located within the distal tip protector, or preferably a an internal cavity thereof, and the method may comprise filling the distal tip protector, or preferably an internal cavity thereof, with fluid.

In other embodiments, the method may not involve such a step. The distal tip protector may be supplied already containing a fluid or, preferably with an internal cavity thereof containing a fluid. Thus, the distal tip protector, or preferably an internal cavity thereof, may be pre-filled i.e. filled prior to supply to the user e.g. during manufacture. The protector may then comprise a sealed fluid containing chamber into which the distal tip may be inserted. In these embodiments a rupturable resilient seal may be provided to seal the fluid within the distal tip protector or internal cavity thereof prior to use of the distal tip protector. A sealed fluid containing chamber may then be provided by cooperation between the rupturable resilient seal and the interior of e.g. an internal cavity of the protector.

It will be appreciated that references to the cavity or protector being filled do not necessarily imply that the cavity or protector is completely filled provided that the cavity or protector is filled in a manner that allows fluid to be maintained around the distal tip of an instrument when located therein.

In other embodiments the method may comprise the step of applying the distal tip protector to the distal tip of an instrument e.g. inserting the distal tip into the distal tip protector or internal cavity, and then supplying fluid to the interior of the distal tip protector or internal cavity e.g. filling the protector or internal cavity.

It may be seen that the method may or may not extend to the step of supplying fluid to the interior of the distal tip protector, or, in preferred embodiments, an internal cavity thereof. The step of supplying fluid, where carried out, may be carried out by a user. Where the method includes a step of supplying a fluid to the distal tip protector or internal cavity thereof this may be carried out before or after application of the distal tip protector to the distal tip of the instrument e.g. insertion of the distal tip into the distal tip protector or an internal cavity thereof. Fluid is preferably supplied before application of the protector to an instrument.

In some embodiments the distal tip protector comprises a fluid inlet to enable fluid to be supplied to the interior of the distal tip protector, and, in preferred embodiments in which the protector comprises an internal cavity, to the interior of the cavity. The method may comprise supplying fluid to the interior of the distal tip protector, or internal cavity, via the fluid inlet. The inlet may be used to supply a fluid to the interior of the protector, or an internal cavity thereof before or after application to a distal tip of an instrument e.g. insertion of the distal tip of the instrument into the protector. The fluid inlet may be used to refill the distal tip protector in embodiments where the protector is reused, whether or not it is initially used to fill the protector. The fluid inlet may be configured to enable fluid to be supplied to the interior of the protector or an internal cavity thereof while the distal tip of an instrument is located therein. In some embodiments only a single fluid inlet is provided. The fluid inlet may be arranged in any manner so as to be in fluid communication with the interior of the protector or an internal cavity thereof which holds the fluid in use, and any intermediate fluid connection may be used. In some preferred embodiments the fluid inlet preferably extends through a wall of the distal tip protector from the interior to the exterior thereof, and preferably extends through the wall of an internal fluid cavity of the distal tip protector to the exterior of the distal tip protector. The fluid inlet may be a port in a wall of the protector.

In some preferred embodiments the fluid inlet is located at a distal end of the distal tip protector, and may be located on a distal end face of the distal tip protector. The fluid inlet is preferably located remote from a resilient seal of the protector. The fluid inlet is additional to any aperture in a resilient seal of the protector.

In some embodiments the distal tip protector may further comprise means for closing the fluid inlet to inhibit fluid from leaking out of the distal tip protector or an internal cavity thereof. The means may be a releasable means which may be removed to provide access to the fluid inlet and replaced to close the fluid inlet as required. The means may comprise a closure element such as a cap, plug or any suitable fitting. In other embodiments the closing means may comprise a one way valve. In other embodiments, it has been found that if the fluid inlet is appropriately configured, it may be possible to avoid the need to provide closure means, as fluid may be retained in the tip protector or internal cavity thereof in a similar manner to that by which liquid may be maintained in a pipette, even when the protector or chamber is inverted, due to the air restriction that is provided by the fluid inlet. In some embodiments the fluid inlet may be configured to inhibit the passage of fluid from the interior of the tip protector or cavity to the exterior of the protector e.g. without the need for a separate closure element.

In embodiments in which a fluid inlet is provided the fluid inlet may be configured for connection to a means for supplying fluid. In some embodiments the fluid inlet comprises a luer type connection. This may enable fluid to be supplied from a device having a cooperating luer type fitting e.g. a syringe. A luer type fitting may be configured appropriately to be fluid tight without the need for a separate closure element. The method may comprise supplying fluid to the fluid inlet using fluid supply means connected thereto e.g. a syringe.

In other embodiments the distal tip protector does not comprise a fluid inlet to allow fluid to be supplied to the interior thereof at least after the distal tip protector has been applied to an instrument e.g. an instrument has been inserted therein, and, in embodiments, before or after application of the distal tip protector to an instrument. The distal tip protector may comprise no fluid inlet at a distal end thereof.

Once removed from the distal tip of an instrument i.e. when the instrument is removed for reprocessing, it is envisaged that the distal tip protector may be reused. In these embodiments the method may comprise removing the distal tip protector from the distal tip of a first instrument, and applying the distal tip protector to a second medical instrument e.g. inserting the second medical instrument into the distal tip protector. In these embodiments, where provided, a resilient seal may conform to the contours of the second instrument to allow fluid to be maintained around the distal tip of the instrument as with the first instrument. The resilience of the seal will allow it to function in this manner even if it is had been ruptured by the first instrument. The resilient seal may be able to suitably conform to instruments of different diameters.

Where the protector is to be reused, it is preferably constructed to allow refilling e.g. by including a suitable fluid inlet, or alternatively, refilling might be achieved via an aperture of the resilient seal e.g. formed by the rupture of the seal by a first instrument, or provided by the initial use of an apertured seal.

In embodiments the method may further comprise supplying fluid to the interior of the distal tip protector or an internal cavity thereof to refill the protector or cavity for providing fluid for contacting the distal tip of the second instrument. This may be carried out after before or after insertion of the second instrument into the tip protector. In other arrangements, it is envisaged that one instrument may be removed from the protector and another inserted without changing the fluid in the protector.

In some further embodiments the distal tip protector may further comprise means for generating heat for heating the fluid in the distal tip protector e.g. in an internal cavity thereof in use when activated. The heat generating means is arranged to heat the fluid around the distal tip of the instrument. In these embodiments the method may comprise activating the means to generate heat for heating the fluid around the distal tip of the instrument. The heat generating means may be arranged to be activated in any suitable manner. For example, the heat generating means may be arranged to be activated as a result of application of the distal tip protector to an instrument e.g. insertion of an instrument into the distal tip protector, or a separate operation may be required.

The heat generating means may be located in any manner with respect to the protector provided that it may heat a fluid therein e.g. within an internal cavity thereof. The heat generating means may or may not be in direct thermal contact with the fluid to be heated provided that it is in thermal communication therewith. For example, it may be located internally or externally of an internal cavity. In embodiments the heat generating means might be located externally of a cavity for transmitting heat through the walls thereof for heating fluid in the cavity.

The heat generating means may be associated with any part of the protector. Preferably the heat generating means is located at a distal end thereof.

The heat may be generated in any suitable manner. The heat is preferably generated via a chemical reaction. In some embodiments the heat may be generated via an exothermic reaction. Suitable systems are used in e.g. heat packs and similar, resulting in the generation of heat when two components are allowed to mix. The step of activating the heat generating means may comprise causing components of the heat generating means to mix in order to provide an exothermic reaction thereby generating heat. The heat generating means may comprise first and second components separated by a barrier, which barrier may be breached e.g. by a user to allow mixing of the components to generate heat via an exothermic reaction. For example the components may be located in separate compartments which may be ruptured to allow mixing of the components. Arrangements in which heat generating means is provided may provide further benefits in pre-treatment of a contaminated instrument by enhancing the pre-cleaning effect of the fluid contacting the distal tip of the instrument, and, in some embodiments, boosting an enzyme activity of a fluid comprising a decontaminating agent that include an enzyme. In preferred embodiments the heat generating means is used in conjunction with a fluid comprising a decontaminating i.e. cleaning agent that comprises an enzyme.

In embodiments in which the distal tip protector comprises an internal cavity for holding fluid, the chamber is preferably an elongate cavity. The cavity extends between the proximal and distal ends of the protector, and may extend to the distal tip thereof. The cavity may extend at least 50%, or at least 75% or preferably at least 90% or an entire length of the distal tip protector. Thus the cavity may have a length corresponding to a length of the protector. The cavity is preferably defined by an interior space of the tip protector, or at least a main body thereof, and preferably corresponds to the entire interior space thereof.

The internal cavity is preferably defined at least in part, and optionally completely by walls of the tip protector. The walls may be external walls. This may provide a particularly simple arrangement, and minimises the number of parts required.

The distal tip protector may define one or more side walls, and a distal end wall. The distal tip protector may further comprise a proximal end wall. At least the side walls and distal walls may be external walls.

In some embodiments the distal tip protector comprises a main body defining the one or more side walls and the distal end wall. The proximal end wall may be provided by a resilient seal of the tip protector. The proximal wall may therefore be closed or may comprise an aperture depending upon the construction of the seal. In preferred embodiments at least the one or more side walls and distal end wall are integrally formed with one another.

In preferred embodiments the distal tip protector comprises a hollow main body, and the internal cavity is defined by the interior space of the main body. This may provide a more space efficient arrangement. However, it is envisaged that the internal cavity may be defined by another component located within the distal tip protector i.e. within an internal space thereof.

In some preferred embodiments the distal tip protector is tubular. In preferred embodiments the distal tip protector comprises a main body in the form of a tube that is closed or substantially closed at a distal end thereof. The main body may have an open proximal end at which the resilient seal is provided. The seal at least restricts the open proximal end, and may close the proximal end.

The walls, at least of the main body of the distal tip protector may be formed of any suitable material. The walls are preferably solid walls. The walls are non porous. The walls are preferably fluid impermeable walls. This enables the walls to define the internal fluid holding cavity of the protector. In embodiments the distal end wall and the one or more side walls of the main body of the protector are formed of a polymeric material or glass. The distal tip protector preferably does not include a sponge (i.e., absorbent) material.

The distal tip protector is elongate. The distal tip protector may be rigid.

The distal end of the distal tip protector, or main body thereof, is configured to protect the distal tip of the instrument. The distal end covers the distal tip of the instrument. Preferably the distal tip protector, or the main body thereof, is closed or substantially closed at the distal end thereof. The distal tip protector may be rounded at a distal end. Preferably the side wall or walls of the main body of the distal tip protector are closed. The closed distal end of the distal tip protector is closed to prevent the passage of fluid therethrough. In some arrangements as described above, however, it is envisaged that a fluid inlet might be provided e.g. in a distal end of the protector. The side wall or walls and distal end wall of the protector may be continuous other than in the region of a fluid inlet of the protector. The fluid inlet may then be closed by a closure means or may be configured to inhibit the passage of fluid out of the interior of the protector to thereby result in the distal end being closed to prevent the passage of fluid therethrough.

The distal tip protector extends over only a portion of the length of the instrument to which it is applied. The distal tip protector may cover only a distal end of the instrument. For example, the distal tip protector may extend less than 30% or less than 25% or less than 15% along the length of an instrument. In embodiments only a distal tip of the instrument is inserted in the distal tip protector. The distal tip protector covers only a distal tip of the instrument. The distal tip refers to a part of the instrument at a distal end thereof.

The distal tip protector may have any suitable dimensions depending upon the instrument with which it is to be used.

The distal tip protector may have a length of at least 50 mm, or at least 60 mm or at least 100 mm. Alternatively or additionally the distal tip protector may have a length of no greater than 300 mm, or no greater than 250 mm or no greater than 240 mm. In some embodiments the length of the distal tip protector is in the range of from 100 mm to 240 mm.

The distal tip protector may have a diameter of at least 5 mm, or at least 10 mm or at least 15 mm. Alternatively or additionally, the distal tip protector may have a diameter of no greater than 40 mm, no greater than 30 mm, or more preferably no greater than 25 mm, or no greater than 20 mm. The diameter may be in the range of from 5 mm to 20 mm. The protector may be suitable for use with instruments of diameter of around 5 mm, around 10 mm or around 15 mm. Such diameters are standard instrument diameters for laparoscopic or similar surgical instruments. For some instruments the protector may have a diameter of no greater than 20 mm, or no greater than 18 mm or no greater than 15 mm. The protector may then have a diameter of at least 5 mm or at least 10 mm.

The length and/or diameter of the distal tip protector may be in any combination of the above ranges and sub ranges. Any one of the length ranges or sub ranges may be combined with any one of the diameter ranges or sub ranges.

The distal tip protector may be of any suitable shape. The protector may be circular in (transverse) cross section. In other arrangements the protector may be of a different cross sectional shape to accommodate different shaped instruments. The protector may be cylindrical in shape.

The distal tip protector may define a single internal cavity for holding fluid.

The distal tip protector may be configured to allow viewing of the distal tip of an instrument therein. Thus it may comprise a viewing window. An internal cavity in which the tip of the instrument is located may comprise transparent walls.

The distal tip protector may be a single piece protector or may comprise multiple sections that are connected together. Where multiple sections are provided, preferably the sections are of differing lengths. In embodiments, protector is provided pre-assembled to the user. However, in other embodiments the protector may comprise a plurality of sections that are assembled by a user to provide the protector. The sections are longitudinal sections. The step of providing the protector may comprise a user assembling the distal tip protector prior to use in the method of the present invention. In some preferred embodiments the distal tip protector comprises a distal end section and one or more further longitudinally extending sections which are assembled proximal thereto to provide the distal tip protector. In this way, the length of the protector may be more readily customised by selecting a suitable section or sections to be attached to the distal end section in providing the protector. The sections are assembled by connecting them in an end to end relationship. The distal end section may be a closed ended section as discussed above. The distal end section may comprise a fluid inlet and/or heat generating means where provided.

In embodiments the or a further longitudinally extending section is a proximal end section. In some embodiments the protector may be a formed by connecting the proximal end section directly to the distal end section. This would provide a two piece protector. In other embodiments the protector may comprise a proximal end section and one or more intermediate section which is used to connect the proximal end section to the distal end section. In preferred embodiments only one intermediate section is provided. The protector may then be a three piece protector. The proximal end section in either embodiment preferably comprises the resilient seal through which an instrument is inserted. The or each intermediate section where provided may be a length of tubing. The tubing is preferably open at both ends. The or each intermediate section may be an unmodified length of tubing. In these arrangements the length of the protector may be varied by selecting a different length intermediate section. The distal and proximal end sections which are adapted to provide the function of the protector e.g. including a resilient seal, fluid inlet etc., can be used with different intermediate sections to obtain a desired length, avoiding the need to change these parts which include the additional functionality.

In two piece embodiments a proximal end section is longer than a distal end section. In embodiments having an intermediate section e.g. 3 piece embodiments, the intermediate section is preferably longer than the proximal or distal end section.

In embodiments the method comprises assembling the sections of the protector where multiple sections are provided in a manner which provides a fluid tight connection between the sections. In embodiments, the sections may be manually fitted together to provide the fluid tight connection. This may be achieved using suitable sealing means associated with one or more of the sections etc., or by an appropriate resilient fit etc. The sealing means may extend circumferentially around the section or sections. The sealing means may comprise a resilient seal. In preferred embodiments in which an intermediate section and proximal and distal end sections are provided, sealing means is associated with each end section. In embodiments the respective longitudinal ends of the intermediate section are located over or within the sealing means of each end section to assemble the device thereby providing a fluid tight connection between the sections. This may allow the intermediate section to be provided by a simple length of tubing without modification. Where the protector is a two piece protector, either piece may comprise sealing means.

In some embodiments the length of the distal tip protector may be customised by selecting one or more of the sections from a plurality of sections of different lengths. In some embodiments in which the protector is provided by assembling at least a first and a second longitudinally extending section together, the method may comprise a user selecting a first section and selecting a second section from a set of a plurality of different length interchangeable second sections and assembling at least the first and the second sections together to provide a protector of a desired length. The method may further comprise selecting a third section and assembling the third section with the first and second sections to provide the protector. The first section may be a distal end section. The second end section may be a proximal end section or an intermediate section where a third section is used. Where a third section is used, the third section may be a proximal end section. The proximal, distal, and, where provided, intermediate section, may be configured in accordance with any of the embodiments described above. In embodiments different ones of the second sections may be assembled with the first section and optionally third section to provide different length protectors. The second sections are interchangeable. For example, different second length second sections may be provided for use with different types e.g. lengths of instrument. Of course more than one third section may be included. A kit may be provided comprising the first section, set of second sections and optionally third section from which the sections are selected by the user.

In embodiments in which the distal tip protector comprises a plurality of sections that are assembled by a user, the sections when combined provide a distal tip protector in accordance with any of the embodiments described herein. The sections together define the main body of the protector, which preferably defines an interior cavity that is used to hold fluid. The sections preferably define a hollow main body. The sections preferably together define a continuous internal space which provides the interior cavity. The entire interior space of the protector formed may therefore be used to contain fluid. The protector may have overall dimensions in any of the ranges described above, and may be formed of any of the materials described.

In embodiments in which the distal tip protector is assembled by a user prior to use, the step of applying the distal tip protector to the instrument may comprise assembling the distal tip protector around the instrument. However, preferably the distal tip protector is assembled before being applied to the instrument. A fluid may be supplied to the interior of the protector during or after assembly thereof. For example, fluid may be supplied to the interior of the protector before a final section e.g. distal section is connected, avoiding the need to provide a specific fluid inlet.

In accordance with the invention in any of its aspects, the distal tip protector defines a longitudinal direction and a transverse direction. The distal tip defines a proximal end and a distal end. Preferably the step of applying the distal tip protector to the instrument comprises inserting the distal tip through a proximal end of the distal tip protector.

In accordance with the invention in any of its embodiments, the fluid may be any suitable fluid. The fluid is a liquid. References to providing a barrier to the passage of fluid, or providing a fluid seal etc. should be understood as providing such a barrier or seal to the passage of liquid. The fluid may be water or may comprise one or more decontaminating agents. A decontaminating agent may be a disinfecting or cleaning agent, and the fluid may comprise one or both type of agent. The fluid may comprise a detergent. A decontaminating agent may comprise an enzyme. For example, a detergent may comprise an enzyme. A user may select the appropriate form of fluid for use in pre-treating a given instrument.

The invention is applicable to any medical instrument having a distal tip that is contaminated and is subsequently to be decontaminated during reprocessing of the instrument. The instrument is an elongate instrument. The instrument may be pencil-like. The instrument may be generally cylindrical in shape. The instrument is longer than the distal tip protector.

In accordance with the invention in any of its aspects, the medical instrument whose distal tip is inserted into the distal tip protector may be of any suitable type. The instrument comprises a proximal end and a distal end comprising the distal tip. The instrument may comprise a shaft connecting the proximal and distal ends thereof. The distal tip may be connected to the shaft. The distal tip preferably is a working end of the instrument. The distal tip may comprise a working portion of the instrument.

The working portion may be of any type having utility in the medical e.g. surgical field. In preferred embodiments the working portion is a surgical working portion. By way of example, the working portion may comprise scissors, a grasper, retractor, stabilizer, cautery implement, clamp, stapler, or needle holder. The working portion might be the working portion of a conventional pair of scissors i.e. the blades thereof. In some embodiments the medical instrument is a surgical instrument for use in robot assisted surgery. In these preferred embodiments, the instrument may comprise a working portion in the form of an end effector. Whatever the nature of the instrument, the working portion may be provided as a separate piece removably attached to the remainder of the medical instrument e.g. to a distal end of a shaft. This may allow interchanging of different types of working portion as desired. The working portion may be arranged to be articulated or actuated in use.

The distal tip of the instrument may or may not comprise parts that are movable relative to one another to actuate a working portion of the instrument. In some embodiments the instrument may comprise a working portion that may be articulated between different positions. The instrument may comprise a working portion connected via a joint e.g. wrist to a shaft of the instrument.

The instrument may comprise an operating portion for remotely controlling operation of a working portion at the distal tip of the instrument. The operating portion may be located at the proximal end of the instrument. The operating portion may be connected to the working portion via an operation transmission means e.g. mechanism, for remotely controlling operation thereof. In some embodiments therefore, the operating portion may be arranged to provide remote control of operation of a working portion via operation transmission means, and comprises an operation interface or handle portion for providing an indication of an operation to be effected at the working portion. The operating portion is then not located in the distal tip protector.

Regardless of how it is operated, the operating portion may be an actuation e.g. articulation transmission means e.g. mechanism for remotely controlling actuation or articulation of a working portion of the instrument, and the interface where provided may be an actuation or articulation transmission interface. The operating portion and, where provided, operation transmission means, preferably comprise or consist of mechanical operating mechanisms or operation transmission mechanisms. In other words, actuation of the operating portion enables remote manipulation of the working portion of the instrument via a mechanical arrangement, and the operating portion may comprise a mechanically operated handle portion or interface.

Where provided, an interface of the operating portion may be manually operable in use of the instrument. The interface may be a user interface. A handle portion would similarly be manually i.e. user operable. The interface or handle portion may comprise one or more wheels, dials, buttons, graspable levers etc. For example, this may be the case for some instruments intended for use in laparoscopic or other minimally invasive techniques, or for simple forceps, scissors or similar. In other arrangements the operating portion or an interface of the operating portion may be intended to be manipulated via a device connected thereto e.g. a robotic manipulator for remotely controlling manipulation of a working portion of the instrument. Examples of such instruments are those used in so-called "robot assisted surgery".

The method and apparatus of the invention may be used in conjunction with any such instrument. In accordance with the invention, the medical instrument may be a laparoscopic instrument, an instrument for use in minimally invasive surgery, an endoscopic instrument, an instrument for use in NOTES, or an instrument for use in robot assisted surgery. The medical instrument may be an instrument used in telesurgery. While the present invention has particular application to more complex surgical instruments, or remotely operated instruments, it will be appreciated that in other arrangements, the medical instrument might be forceps, scissors or other such instruments having a working portion at a distal end thereof. However, the invention is also applicable to instruments that do not have a remotely operated working portion at a distal tip thereof, or to more simple probe like devices.

The proximal end of the protector is the end closest to the user in use, through which the distal tip of the device is inserted, and the distal end is the end furthest from the user i.e. the end which covers the distal tip of the instrument.

The method of the invention may involve providing and/or using a protector in accordance with the construction described herein e.g. using the seal, inserting the instrument through the seal, etc.

For the avoidance of doubt, the present invention in accordance with any of the aspects described herein may include any or all of the features described by reference to any other aspect of the invention to the extent that they are not mutually exclusive.

BRIEF DESCRIPTION OF THE DRAWINGS

Some preferred embodiments of the invention will now be described by way of example only and by reference of the accompanying drawing of which;

FIG. 1 is an exploded view of a distal tip protector in accordance with a first embodiment which may be used in the methods of the present invention;

FIG. 2A is an exploded view of an alternative embodiment of a distal tip protector which may be used in the methods of the invention;

FIG. 2B is a detail showing the connection of the distal end section to the intermediate section of the distal tip protector shown in FIG. 2A;

FIG. 3 is an exploded view of a distal tip protector in accordance with a further embodiment, and which may be used in the methods of the present invention;

DETAILED DESCRIPTION

Figure 4:
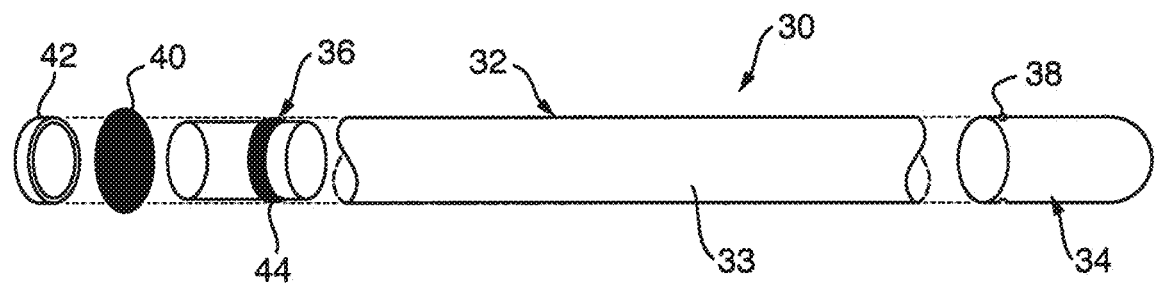
FIG. 4 is an exploded view of yet another embodiment of a distal tip protector which may be used in the methods of the invention described herein.

Referring to FIG. 1, a distal tip protector in accordance with one embodiment and which may be used in the methods of the invention is designated 1, and includes a main body 3 in the form of a tube that is closed at a distal end 5 thereof. The tube is similar in construction to a test tube. The main body 3 is formed of a suitable rigid material, such as a plastics material or glass. At the proximal end 7 of the main body, a rupturable resilient seal 9 is provided, closing the proximal end 7. FIG. 1 shows the protector 1 in an exploded view without the resilient ruptureable seal 9 being attached to the proximal end 7 of the tube 3. The seal will be attached to the proximal end 7 to define a fluid tight container with the main body to provide the protector that is used in the methods of the invention. This attachment occurs before the protector is supplied to a user. The seal may be of any suitable resilient material which may conform to the contours of an instrument inserted therethrough in use after rupture to provide a barrier to the passage of fluid between the seal and the instrument. The seal also cooperates with the instrument to grip the instrument and maintain the protector attached thereto. For example, the seal may be a polymeric material, such as a cling film type material. In the illustrated embodiment the seal is in the form of a disc shaped liquid impermeable membrane.

The main body 3 defines a longitudinal side wall and a distal end wall, which are integrally formed with one another. The main body defines an interior space which provides an interior cavity 11 which is filled by a fluid. The fluid is a decontaminating fluid in the form of a liquid, and may be water, or may additionally include one or more decontaminating agents. The seal 9 seals the proximal end of this cavity to provide a fluid tight container.

The distal tip protector further comprises an end cap 13 which is used to protect the seal 9 before use of the distal tip protector.

The distal tip protector has a length L and a diameter d.

FIG. 2A illustrates another embodiment of distal tip protector 10 that may be used in the methods of the invention, and which is similar to that shown in FIG. 1, but is comprises two separate longitudinal sections. The distal end section 12 is connected to a proximal end section 14 to provide the main body of the protector 10. The sections 12, 14 are assembled to one another by a user. A seal 16, which may be in a form of a O-ring seal or similar, provides a fluid tight connection between the sections 12 and 14.

As in the embodiment of FIG. 1, a ruptureable seal 18 is provided at the proximal end of the proximal end section 14, which is protected by an end cap 19.

Again, the seal 18 is shown in an exploded view, and will be connected to the proximal end of the section 14 to seal the end of an internal cavity 13 defined by the main body of the protector and provide a fluid container, this time with the main body being defined by the sections 12 and 14 when connected together. A fluid is present in this internal cavity 13 in the use of the protector. The interior spaces of the two sections 12 and 14 define a continuous internal cavity of the main body. The seal is attached to the proximal end of the proximal end section 14 before the end section is supplied to a user.

FIG. 2B is a detailed view showing the connection of the distal end section 12 to the proximal end section 14, by means of the resilient seal 16. It can be seen that the proximal end of the distal end section 12 is pushed into the distal end of the proximal end section 14. Alternative arrangements might be used to achieve a fluid tight connection e.g. by use of a resilient fit etc.

In embodiments of the type shown in FIG. 2A or B, the distal tip protector can be filled with a fluid by a user before use. For example, a user might fill the section 14 from the distal end thereof before assembling the distal end section 12 thereto to provide a container for the fluid.

FIG. 3 illustrates yet another embodiment of a distal tip protector which may be used in accordance with the invention. A distal tip protector 20 this time is of a similar two-piece construction to that shown in FIG. 2A, having a proximal end section 22 and a distal end section 24 which are connected to one another by a user via seal 26 to provide a fluid tight connection therebetween in a similar manner to that described by reference to FIGS. 2A and 2B.

Once again a proximal end of the proximal end section 22 is sealed by a ruptureable seal 28, which is shown in an exploded view in FIG. 3, but is attached to the proximal end section before it is supplied to a user, and a cap 29 is provided to protect the ruptureable seal 28.

When the sections 22 and 24 are assembled to one another, the sections provide a main body that defines an interior space providing an internal cavity 23 which contains a fluid during use of the protector. The proximal end of the cavity 23 is sealed by the seal 28 to provide a fluid holding container.

The embodiment of FIG. 3 differs from that of FIGS. 2A and 2B in the construction of the distal end section 24. Rather than having a closed distal end, this includes a fluid inlet 27 in the form of a luer type connection, through which fluid may be supplied into the internal space defined by the main body provided when the sections 22 and 24 have been assembled to one another e.g. using a syringe.

Although not shown in FIG. 3, a cap or other closure element may be located over the fluid inlet 27 once fluid has been provided to the interior of the protector to provide a seal resisting the passage of liquid out of the inlet once more. In other arrangements the inlet 27 might include a one-way valve, or, it is envisaged that it is of the construction shown in FIG. 3, the inlet might be left open. In a similar manner to that involved with the operation of a pipette, the inlet of this configuration might provide an air restriction that would allow fluid to be retained in the main body of the protector even when inverted.

In this embodiment the protector may be filled with fluid before or after connection of the distal and proximal end sections to one another.

In FIG. 4, a further embodiment of the distal tip protector which may be used in accordance with the invention is shown. The distal tip protector 30 is this time made up of three longitudinal sections, a distal end section 34, and proximal end section 36, and an intermediate section 32. The sections are connected to one another by a user in a manner similar to that described by reference to FIGS. 2A and 2B by means of seals 38 and 44 associated with the distal and proximal end sections 34 and 36 respectively. The intermediate section 32 has ends which are slid over the seals associated with the distal and proximal end sections respectively to provide a fluid tight connection thereto in a manner similar to that described by reference to FIG. 2B.

When the sections 32, 36 and 34 are assembled together, they provide a main body defining a continuous interior space that provides an internal cavity 33 which holds fluid in use. At the proximal end of the proximal section 36, a rupturable seal 40 is provided which is located over the open end to close the proximal end of the internal cavity 33 to define a fluid holding container. An end cap 42 is provided for protecting the seal 40.

The protector of the FIG. 4 embodiment may be filled with fluid by a user before assembling the proximal end section to the assembled distal and intermediate sections, or before assembling the distal end section to the assembled proximal and intermediate sections.

The embodiments of FIGS. 2A, 2B, 3 and 4 provide the ability to more readily customise the length of the distal tip protector. For example, in the embodiments of FIG. 2A or B or FIG. 3, a user might take a standard distal end section, and connect it to a different length proximal end section or visa-versa. In FIG. 4, the length of the intermediate section 32 may be varied by interchanging the intermediate section 32 with one of different length to provide different lengths of protector. As the intermediate section 32 is, in the FIG. 4 arrangement, a simple a length of tubing, a user may readily be able to substitute tubing of a different length. For example a kit might be provided including the proximal and distal end sections in the FIG. 4 embodiment and different length intermediate sections which can be interchangeably used with the proximal and distal end sections.

The use of the distal tip protector in accordance of the embodiment of FIG. 1 will now be described by reference to FIG. 5.

The method will be described by reference to the pre-treatment of a contaminated surgical instrument 50 having a distal tip 52. The distal tip 52 includes a working portion which is connected to a shaft 54 of the instrument via a wrist 53. The working portion is the part of the surgical instrument which interacts with the body, and includes various moving parts whose surfaces may become contaminated e.g. with tissue or blood during use. The method is a method of pre-cleaning of the surgical instrument before the instrument undergoes full reprocessing step e.g. decontamination such as may include deluge cleaning, ultra-sonic cleaning, sterilisation, disinfection or any other cleaning processes, whether carried out manually or automatically to render the instrument suitable for reuse. The instrument is one which has been used in a surgical procedure. The method of pre-cleaning may be carried out in the operating theatre.

A user removes the end cap 13 from the proximal end of the main body 3 of the protector 1. This exposes the ruptureable seal 9 which closes the proximal end of the main body, and co-operates with the internal cavity 11 of the main body to hold a decontaminating fluid.

The user of the surgical instrument pushes the distal tip 52 through the ruptureable seal 9 into the internal cavity 11, thereby bringing it into contact with the decontaminating fluid therein. Once the surgical instrument has been inserted in the protector, it will be as shown in FIG. 5. When the surgical instrument is disposed in the protector, the protector 5 serves a dual function of protecting the delicate distal tip 52 from harm, and also surrounding it by a decontaminating fluid which is able to come into contact with the surfaces thereof to provide a pre-treatment of the distal tip before it undergoes full reprocessing e.g. decontamination.

The resilient seal 9 cooperates with the shaft of the instrument 54 to grip the shaft and retain the distal tip in the protector, and also to provide a barrier to the passage of fluid out of the cavity 11 around the instrument. This enables the protector to remain attached to the instrument, and maintain fluid around the distal tip thereof, until it is removed by a user e.g. to allow the instrument to undergo decontamination. The resilient seal is formed of a material which allows it to conform to the contours of an instrument inserted therethrough in use to provide a fluid resistant seal therearound.

The distal tip protector is kept in position located over the distal end of the instrument until it undergoes reprocessing. This may be during storage or transport of the instrument e.g. from a site of use to a reprocessing facility. In this way, the working end of the instrument is kept moist by the fluid surrounding it, facilitating subsequent decontamination thereof, avoiding contaminants becoming coalesced and dried to the surfaces of the instrument.

Figure 5:
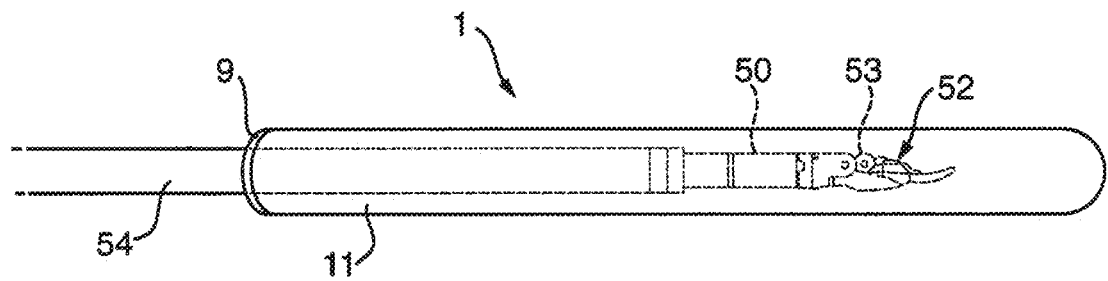
FIG. 5 illustrates the use of a distal tip protector of the type shown in FIG. 1 in accordance with the methods of the present invention to pre-treat an instrument.

Once a distal tip protector of the type shown in FIG. 5 has been used to pre-treat an instrument, and the instrument removed therefrom for re-processing e.g. decontamination, it is envisaged that the distal tip protector could be reused. When the protector is of the type shown in FIG. 5, the seal 9 will have been ruptured. However, as it is resilient, it may conform to the contours of another instrument when subsequently located therein to retain the instrument and prevent the passage of fluid out of the proximal end of the protector. In these arrangements, the same decontaminating fluid might be reused, or more usually the chamber 11 will be refilled. This could be achieved by providing a suitable fluid inlet for the purposes of refilling, which may be as shown e.g. in FIG. 3. The same inlet might be used to provide an initial filling of the chamber if required. Alternatively, it is envisaged that fluid might be introduced into the internal cavity 11 via the ruptured seal 9 before a new instrument is inserted therein.

Figure 6:
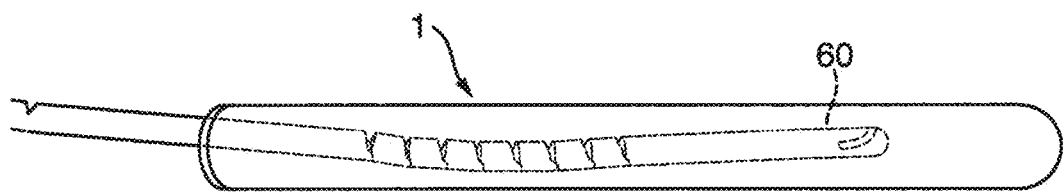
FIG. 6 illustrates the use of the distal tip protector of FIG. 1 in the pre-treatment of an alternative type of medical instrument.

FIG. 6 illustrates a similar arrangement involving a use of the tip protector shown in FIG. 1 but in conjunction with a different type of surgical instrument 60.

Of course the distal tip protector may be used in conjunction with numerous types of instrument, and those shown in FIGS. 5 and 6 are merely exemplary. Where the working portions of the instrument extends further along the length of the instrument, a longer distal tip protector might be required.

In the embodiments of FIGS. 5 and 6, the instrument is inserted into the internal fluid filled cavity 3 through the ruptureable seal 9. Thus the cavity contains a fluid before the instrument is inserted therein, and before supply to a user.

As mentioned above, in other embodiments a user may fill the protector i.e. the internal cavity thereof themselves, rather than the protector being supplied in a pre-filled form. This may be achieved by filling the internal cavity via a fluid inlet where provided, for example at a distal end in a manner shown in FIG. 3. Such an inlet could be incorporated in single section distal tip protector along the lines shown in FIG. 1. The user may then locate a suitable closure means over the fluid inlet to ensure that the fluid remains in the fluid chamber during treatment of an instrument if necessary.

Operation of the embodiment shown in FIG. 2A is similar to that of FIG. 1. In addition, the user assembles the sections 12 and 14 to one another before use of the protector. The user will push the distal end of the proximal end section 14 over the seal 16 associated with the distal end section to obtain a distal tip protector which then may be used in the same manner as that of FIG. 1. This embodiment provides the option for the user to fill the protector themselves by supplying a fluid to the interior of the section 14 before it is closed by assembling it to the distal end section 12.

The embodiment of FIG. 3 may be used in the same manner as that of FIGS. 2A and 2B. As previously described, the user must assemble the sections 22 and 24 to one another to obtain the protector before inserting an instrument therein. In this case, the user may then fill the internal space 13 defined within the main body once assembled using the fluid inlet 27 e.g. by connecting a syringe thereto. The user may or may not then locate a suitable closure over the inlet 27, depending upon the configuration of the inlet, or whether it comprises an integral closure, such as a one way valve.

The embodiment of FIG. 4 may be used in a similar manner to that of FIGS. 2A and B and FIG. 3, with the user additionally needing to assemble the sections 32 and 36 to one another, as well as connecting the sections 32 and 34. This is achieved by pushing the proximal end of the intermediate section 32 over the seal 44 associated with a proximal end section 36, as well as pushing its distal end over the seal 38 associated with the distal end section 34. In this arrangement, fluid may be introduced into the internal cavity defined by before the proximal or distal end section is assembled to the other two sections.

Figure 7:
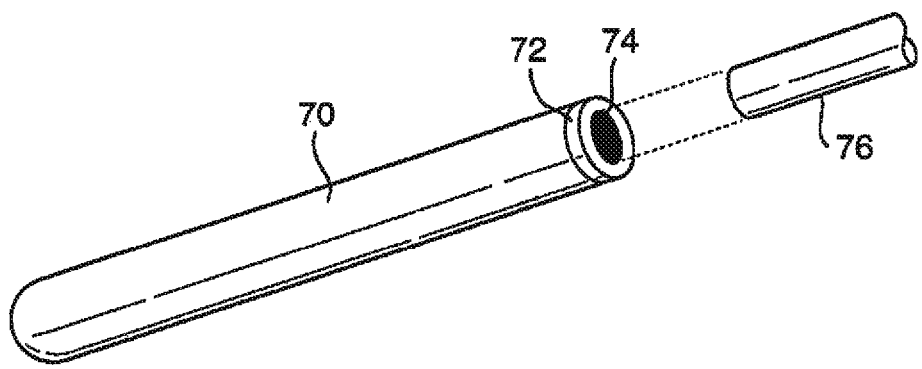
FIG. 7 is an exploded view of a distal tip protector in accordance with a further embodiment of the invention, including guide means for guiding the distal tip of an instrument during insertion.
Figure 8:
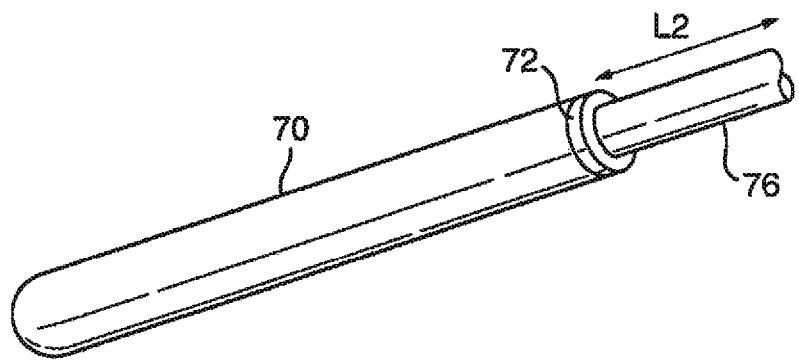
FIG. 8 is a schematic view of the embodiment of FIG. 7.
Figure 9:
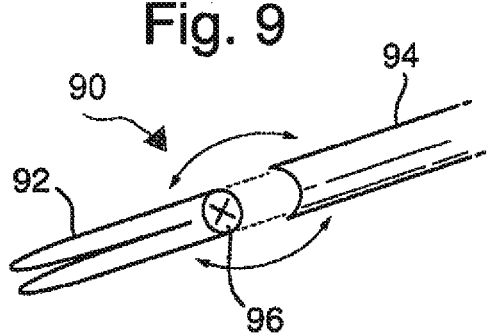
FIG. 9 is a schematic view of the distal tip of an instrument with which the embodiment of FIGS. 7 and 8 may advantageously be used.

FIGS. 7 to 9 illustrate an alternative embodiment of a distal tip protector 70 which includes guide means for guiding the distal tip of an instrument as it is inserted into the distal tip protector. The distal tip protector may be in the form of any of the embodiments described earlier, although, for ease of reference is shown as having a single piece main body. For example, the seal and construction of the main body may be of any of the forms previously described. However, in this embodiment, the end cap 72 which protects rupturable seal 74 defines a central aperture. The end cap 72 may therefore remain in place during and after insertion of an instrument in the distal tip protector 70. The end cap will help to retain the seal in place and provide some protection of the seal, covering the radially peripheral parts thereof. It will be appreciated that an end cap of this construction may be used in any of the other embodiments described herein, even those which do not include guide means, as an alternative to an end cap that is removed before use.

FIG. 7 is an exploded view to facilitate understanding of the construction of the device, which shows how the guide means 76, which is in the form of tube having two open ends, is attached to the end cap 72 around the seal 74 so as to project proximally therefrom. FIG. 8 shows the guide means 76 as it appears in the product, attached to the end cap 72 around the central aperture of the end cap. For example, the guide means may be integrally moulded with the end cap, or provided as a separate component attached thereto. The guide means may have a length L2 in the range of from 20-30 mm, for example. The guide means has an internal diameter slightly greater than that of an instrument to be inserted. For example, the diameter may be 9 mm to accommodate an 8 mm diameter instrument. In use, the distal tip of an instrument is inserted through the guide means in order to rupture the seal, before being inserted into the main body of the protector as described in the previous embodiments. The guide means helps to prevent buckling or kinking of the distal tip as it is pushed against the seal to rupture the seal. The guide means remains in place after insertion of the instrument and during use of the distal tip protector.

FIG. 9 illustrates schematically the distal tip of an instrument 90 with which the embodiment of FIGS. 7 and 8, incorporating guide means, may advantageously be used.

The instrument 90 has a distal tip including parts 92 and 94 which may tend to buckle about joint 96 if the tip of part 92 is pushed against a seal. The guide means may inhibit such buckling. The guide means is particularly useful in the context of protectors for use with such instruments.

Although the embodiments described use a rupturable resilient seal at the proximal end of the protector, it is envisaged that an apertured resilient seal could be used. Such a seal may still co-operate with an instrument when inserted therethrough in use to provide a suitable barrier to the passage of fluid out of the proximal end of the protector. In such arrangements, filling of the fluid holding chamber would need to occur after insertion of the medical instrument therein.

Although not shown in the illustrated Figures, heat generating means may be associated with the distal tip protector to provide heating of a fluid located in the internal cavity in use. This may enhance the effects of the fluid, particularly where it comprises enzyme containing decontaminating agents. Heat generating means may generate the heat via an exothermic reaction. Suitable components for generating heat via an exothermic reaction when mixed may be located e.g. to the exterior of a distal end of the distal tip protector, and may be activated to bring the components into contact with one another by a user. This might be via a simple manual action such as a squeezing action or similar, as used with heat packs. In other arrangements, exothermic heat generating means might be arranged to be activated when an instrument is inserted into the protector.

The distal tip protector in accordance with the invention of any of its embodiments may be of any suitable length. The total length may range from around 50 mm to 300 mm. In preferred embodiments the length of the protector is from 100 mm to 240 mm. The length of the main body of the protector is marked "L" in FIG. 1. Where the protector is formed of multiple sections that are assembled to one another, this is the combined length of the sections after assembly. The tip protector may have a diameter of e.g. 5 mm or around 10 mm or around 15 mm depending upon the type of instrument with which it is to be used. The diameter d is marked in FIG. 1.

Rather than using seals of the type shown in FIG. 2B, in those arrangements in which the distal tip protector is formed of multiple sections, these sections may simply be resiliently fitted together without a use of a specific sealing element.

The invention is particularly applicable to more complex instruments such as those used in key-hole surgery, minimally invasive procedures, laparoscopic procedures, robotic surgery, incisionless surgery or NOTES surgery, but may be applied to other types of instrument.

Although the present invention has been described with reference to preferred embodiments, it will be understood by those skilled in the art that various changes in form and detail may be made without departing from the scope of the invention as set forth in the accompanying claims.

The invention claimed is:

1. A distal tip protector for use in pre-treating a contaminated medical instrument that is to undergo reprocessing, the distal tip protector comprising:
   an internal cavity for placing fluid in contact with a distal tip of a medical instrument inserted in the distal tip protector when the distal tip protector is applied to the distal tip of the instrument in use;
   wherein the distal tip protector is pre-filled with fluid to form a sealed chamber of fluid into which the distal tip of the instrument can be inserted, the fluid comprising a detergent or a decontaminating agent;
   a rupturable seal for closing an end of the sealed chamber, the sealed chamber being adapted to receive the distal tip of the instrument inserted through the rupturable seal, wherein the sealed chamber is defined by walls made of a rigid material; and
   an end cap formed as a unitary structure for retaining the rupturable seal in place, said end cap having a central aperture.

2. The distal tip protector of claim 1, wherein the rupturable seal is arranged to conform to a contour of the instrument to inhibit leakage of fluid from the sealed chamber when the distal tip is located in the distal tip protector and comprises a rupturable membrane.

3. The distal tip protector of claim 1, wherein the rupturable seal comprises foil, or a polymeric material.

4. The distal tip protector of claim 1, further comprising a guide extending from a proximal end thereof for guiding an instrument during insertion of the distal tip of the instrument into the distal tip protector.

5. The distal tip protector of claim 1, wherein said end cap protects the rupturable seal prior to use.

6. The distal tip protector of claim 1, wherein the internal cavity of the distal tip protector extends at least 90% of a length of the distal tip protector.

7. The distal tip protector of claim 1, wherein the distal tip protector is tubular and comprises a main body in the form of a tube that is closed or substantially closed at a distal end thereof and open at a proximal end at which the rupturable seal is provided.

8. The distal tip protector of claim 7, wherein walls of the main body of the distal tip protector are formed of a polymeric material.

9. The distal tip protector of claim 1, wherein the distal tip protector has a length of at least 50 mm.

10. The distal tip protector of claim 1, wherein the distal tip protector has a length of at least 60 mm.

11. The distal tip protector of claim 1, wherein the distal tip protector has a length of at least 100 mm.

12. The distal tip protector of claim 1, wherein the distal tip protector has a length that is no greater than 300 mm.

13. The distal tip protector of claim 1, wherein the distal tip protector has a length that is no greater than 250 mm.

14. The distal tip protector of claim 1, wherein the distal tip protector has a length that is no greater than 240 mm.

15. The distal tip protector of claim 1, wherein the rupturable seal is in an unruptured state after the distal tip protector is pre-filled with fluid.

* * * * *